(12) United States Patent
Naasani

(10) Patent No.: US 8,092,859 B2
(45) Date of Patent: Jan. 10, 2012

(54) SYNTHESIS OF HIGHLY LUMINESCENT COLLOIDAL PARTICLES

(75) Inventor: Imad Naasani, Manchester (GB)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/563,900

(22) Filed: Sep. 21, 2009

(65) Prior Publication Data

US 2010/0075437 A1 Mar. 25, 2010

Related U.S. Application Data

(63) Continuation of application No. 11/206,403, filed on Aug. 17, 2005, now abandoned.

(60) Provisional application No. 60/602,271, filed on Aug. 17, 2004.

(51) Int. Cl.
*B05D 7/00* (2006.01)

(52) U.S. Cl. ........ 427/201; 427/203; 427/205; 427/215; 427/220; 977/882; 977/896

(58) Field of Classification Search ................... 428/403; 427/201, 203, 205, 215, 220
See application file for complete search history.

(56) References Cited

U.S. PATENT DOCUMENTS

| | | | |
|---|---|---|---|
| 4,642,334 A | 2/1987 | Moore et al. | |
| 4,946,778 A | 8/1990 | Ladner et al. | |
| 5,006,331 A | 4/1991 | Gaskin | |
| 5,034,506 A | 7/1991 | Summerton et al. | |
| 5,079,010 A | 1/1992 | Natterer | |
| 5,087,442 A | 2/1992 | Takaichi et al. | |
| 5,151,507 A | 9/1992 | Hobbs, Jr. et al. | |
| 5,187,085 A | 2/1993 | Lee | |
| 5,505,928 A | 4/1996 | Alivisatos et al. | |
| 5,558,991 A | 9/1996 | Trainor | |
| 5,596,086 A | 1/1997 | Matteucci | |
| 5,602,240 A | 2/1997 | De Mesmaeker et al. | |
| 5,637,258 A | 6/1997 | Goldburt | |
| 5,679,785 A | 10/1997 | Engels | |
| 5,736,137 A | 4/1998 | Anderson | |
| 5,789,157 A | 8/1998 | Jensen et al. | |
| 5,948,386 A | 9/1999 | Katti | |
| 5,969,135 A | 10/1999 | Ramasamy | |
| 5,990,479 A | 11/1999 | Weiss et al. | |
| 6,114,038 A | 9/2000 | Castro et al. | |
| 6,179,912 B1 | 1/2001 | Barbera-Guillem et al. | |
| 6,221,602 B1 | 4/2001 | Barbera-Guillem et al. | |
| 6,261,779 B1 | 7/2001 | Barbera-Guillem et al. | |
| 6,306,610 B1 | 10/2001 | Bawendi et al. | |

(Continued)

FOREIGN PATENT DOCUMENTS

EP 0990903 A1 4/2000

(Continued)

OTHER PUBLICATIONS

Chan, Prendergast, Jain, and Nie, One-step conugation of Biomolecules to Luminescent Nanocrystals,Molecular Imagine: Reporters, Dyes, Markers, and Instrumentation, Proceedings of SPIE, vol. 3924 (2000).*

(Continued)

*Primary Examiner* — Hoa (Holly) Le

(57) ABSTRACT

The present invention includes compositions and methods for their used wherein the compositions include clusters of coated fluorescent nanocrystals having a select size formed by controlled aggregation of individual coated nanocrystals.

10 Claims, 2 Drawing Sheets

U.S. PATENT DOCUMENTS

| | | | |
|---|---|---|---|
| 6,306,736 | B1 | 10/2001 | Alivisatos et al. |
| 6,319,426 | B1 | 11/2001 | Bawendi et al. |
| 6,361,944 | B1 | 3/2002 | Mirkin et al. |
| 6,475,501 | B1 | 11/2002 | Kelly et al. |
| 6,501,091 | B1 | 12/2002 | Bawendi et al. |
| 6,869,545 | B2 | 3/2005 | Peng et al. |
| 6,872,249 | B2 | 3/2005 | Peng et al. |
| 6,955,855 | B2 * | 10/2005 | Naasani ................ 428/403 |
| 7,198,847 | B2 | 4/2007 | Naasani |
| 7,205,048 | B2 | 4/2007 | Naasani |
| 7,214,428 | B2 * | 5/2007 | Naasani ................ 428/403 |
| 7,309,525 | B2 * | 12/2007 | Reiss et al. .............. 428/403 |
| 7,368,086 | B2 * | 5/2008 | Naasani ................ 422/82.08 |
| 2002/0028254 | A1 | 3/2002 | Nonotte et al. |
| 2003/0059635 | A1 * | 3/2003 | Naasani ................ 428/473.5 |
| 2003/0069171 | A1 | 4/2003 | Petito et al. |
| 2004/0110220 | A1 | 6/2004 | Mirkin et al. |
| 2004/0247861 | A1 | 12/2004 | Naasani |
| 2006/0014175 | A1 | 1/2006 | Naasani |

FOREIGN PATENT DOCUMENTS

| | | |
|---|---|---|
| GB | 2376886 A | 12/2002 |
| WO | WO 96/19182 | 6/1996 |
| WO | WO 98/04740 | 2/1998 |
| WO | WO 98/33070 | 7/1998 |
| WO | WO 2004/039830 | 5/2004 |

OTHER PUBLICATIONS

Adair, John R., *Immunol. Rev.* 130:5-40 (1992).
Aldana et al., *J. Am. Chern. Soc.* 123(36):8844-8850 (2001).
Bruchez Jr. et al., *Science* 281:2013-2016 (1998).
Bunda et al., *J. Biol. Chem.*, 280(3):2341-2351 (2005).
Business Communications Co., *Optical Materials and Engineering News* 5(12):1-2 (1995).
Chan et al., *Science* 281:2016-2018 (1998).
Chan et al., *Proc. SPIE* 3924(2):2-9 (2000).
Dabbousi et al., *J. Phys. Chem. B.* 101(46):9463-9475 (1997).
Danek et al., *Chem. Mater.* 8(1):173-180 (1996).
Efros et al., *Phys. Rev. B.* 54:4843-4856 (1996).
Empedocles et al., *Phys. Rev. Letters* 77(18):3873-3876 (1996).
Fu et al., *Colloids and Surfaces A: Physicochemical and Engineering Aspects* 174(3):367-373 (2000).
Galt et al., *Bioconjug Chem.* 12:354-363 (2001).
Giuliano et al., *Trends in Biotechnology* 16(3):135-140 (1998).
Hines et al., *J. Phys. Chem.* 100(2):468-471 (1996).
Kho et al., *Biochemical and Biophysical Research Communications* 272(1):29-35 (2000).
Murakoshi et al., *J. Colloid Interface Sci.* 203:225-228 (1998).
Murray et al., *American Association for the Advancement of Science* 270(5240):1335-1338 (1995).
Murray et al., *J. Am. Chem. Soc.* 115(19):8706-8715 (1993).
Nirmal et al., *Nature* 383:802-804 (1996).
Norris et al., *Phys. Rev. B.* 53(24):16338-16346 (1996).
Peng et al., *J. Am. Chem. Soc.* 119(30):7019-7029 (1997).
Plückthun, *Immunol. Rev.* 130(1):151-188 (1992).
Rodriguez-Viejo et al., *Appl. Phys. Lett.* 70(16):2132-2134 (1997).
Sacra et al., *J. Chern. Phys.* 103:5236-5245 (1995).
Seyama et al., *Internat. J. Vit. Nutr. Res.* 58(2): 231-235 (1988).
Singer et al., *J. Immunol.* 150(7):2844-2857 (1993).
Stankova et al., *J. Peptide Sci.* 5(9):392-398 (1999).
Tinker et al., *Biochem. J.* 236:17-23 (1986).
Tsiavaliaris et al., *Synlett* 3:391-393 (2001).
Vaxman et al., *Eur. Surg. Res.* 28(4):306-314 (1996).

* cited by examiner

SYNTHESIS OF HIGHLY LUMINESCENT COLLOIDAL PARTICLES

CROSS REFERENCE TO RELATED APPLICATIONS

This application is a continuation of U.S. patent application Ser. No. 11/206,403, filed Aug. 17, 2005 now abandoned, which claims the benefit of and priority to U.S. Provisional Application Ser. No. 60/602,271 filed Aug. 17, 2004, the contents of which are incorporated herein by reference in their entirety.

BACKGROUND

Fluorescence-based analyses and nonisotopic detection systems have become a powerful tool for scientific research and clinical diagnostics for the detection of biomolecules using various assays including, but not limited to, flow cytometry, nucleic acid hybridization, DNA sequencing, nucleic acid amplification, immunoassays, histochemistry, and functional assays involving living cells. Fluorescent semiconductor nanocrystals have found widespread use due to their high fluorescent intensity and the ability of different nanocrystals to be excited by a single light source. It would be desirable to increase the signal from these non-isotopic materials to increase the sensitivity of a variety of assays and analyses utilizing them. It would be advantageous to controllably link numbers of nanocrystals and other small particles into structures for analytical applications that can be used to label a target molecule to be detected.

Mirkin et al, in WO 98/04740 discloses nanoparticles having oligonucleotide attached to them. Methods are disclosed that comprise contacting a nucleic acid with one or more types of nanoparticles having oligonucleotides attached to them. The oligonucleotides are attached to nanoparticles and have sequences complementary to portions of the sequence of the nucleic acid. A detectable change, a color change, is brought about as a result of the hybridization of the oligonucleotides on the nanoparticles to the nucleic acid. The compositions disclosed do not include core/shell semiconductor nanocrystals and use oligonucleotides, specifically complementary oligonucleotides, to form conjugates of the nanoparticles.

Mirkin et al. in U.S. Pat. No. 6,361,944 disclose nanoparticles having oligonucleotides attached to them and uses for the compositions. Again, the disclosure provides oligonucleotides attached to nanoparticles that include core/shell semiconductor nanocrystals and where the oligonucleotide sequences are complementary to portions of the sequence of a nucleic acid to be detected. A detectable change is brought about as a result of the hybridization of the oligonucleotides on the nanoparticles to the nucleic acid. The disclosure purports to illustrate the formation of nanoparticle aggregates, nanomaterials, and nanostructure by combining nanoparticles having complementary oligonucleotides attached to them, the nanoparticles being held together in the aggregates as a result of the hybridization of the complementary oligonucleotides.

Hansen et al. in WO 98/33070 disclose a homogeneous binding assay. The disclosure describes a homogeneous method of measuring chemical binding that relies on resonant, or "amplified", optical extinction (light scattering plus absorption) from a defined, specific class of colloidal particles where the real term n of the complex refractive index n-ik approaches zero while the imaginary term k approaches $2^{(1/2)}$. Chemical binding partners are coated onto the particles, which either aggregate or disperse during the binding reaction, causing an optical extinction change at one wavelength that is quantitatively related to the number of single colloidal particles and another at a second wavelength that is quantitatively related to the number of doublet colloidal particles. The disclosure describes the uses of optical extinction to measure the formation of particle dimers (through the appearance of increased extinction at the split resonant wavelength) and the concomitant disappearance of the singlet particles (through the decrease of extinction at the original resonant wavelength).

Bawendi et al. in EP0990903 disclose biological applications of semiconductor nanocrystals. The disclosure describes compositions comprising fluorescent semiconductor nanocrystals associated to a compound, where the nanocrystals have a characteristic spectral emission that is tunable to a desired wavelength by controlling the size of the nanocrystal, and where the emission provides information about a biological state or event.

Barbera-Guillem et al in U.S. Pat. No. 6,261,779 discloses nanocrystals having polynucleotide strands and their use to form dendrimers in a signal amplification system. The disclosure provides compositions and assay kits comprising functionalized nanocrystals having a plurality of polynucleotide strands of known sequence extending from them. The disclosure describes primary dots that are used to operably link to a molecule, and secondary dots comprise a plurality of polynucleotide strands which are complementary to the plurality of polynucleotide strands of the primary dots. The disclosure provides a method for detecting the presence or absence of target molecules in a sample comprising operably linking primary dots to molecules, contacting the complex formed with the sample, contacting the sample with successive additions of secondary dots and primary dots. If a target molecule is present in the sample, the primary dots and secondary dots will form dendrimers that can be detected by fluorescence emission.

Peng et al. U.S. Pat. No. 6,872,249 disclose the synthesis of colloidal nanocrystals. A method of synthesizing colloidal nanocrystals is disclosed using metal oxides or metal salts as a precursor. The metal oxides or metal salts are combined with a ligand and then heated in combination with a coordinating solvent.

Peng et al. U.S. Pat. No. 6,869,545 discloses colloidal nanocrystals with high photoluminescence quantum yields and methods of preparing the same. The disclosure provides compositions containing colloidal nanocrystals with high photoluminescence quantum yields, synthetic methods for the preparation of highly luminescent colloidal nanocrystals, as well as methods to control the photoluminescent properties of colloidal nanocrystals.

Bawendi et al. in U.S. Pat. No. 6,306,610 disclose quantum dot white and colored light emitting diodes. The disclosure describes an electronic device comprising a population of quantum dots embedded in a host matrix and a primary light source which causes the dots to emit secondary light of a selected color, and a method of making such a device. The size distribution of the quantum dots is chosen to allow light of a particular color to be emitted from the structure. The dots can be composed of an undoped semiconductor such as CdSe, and may optionally be overcoated to increase photoluminescence. The host matrix for the device includes isolated dots within the matrix and not defined aggregates of nanocrystals.

U.S. Pub. No. 20040110220 to Mirkin et al. discloses nanoparticles having oligonucleotides attached to them and uses for such coated nanoparticles. The disclosure provides methods of detecting a nucleic acid that comprise contacting the nucleic acid with one or more types of nanoparticles having oligonucleotides attached to them. The disclosure describes a method where oligonucleotides are attached to nanoparticles and have sequences complementary to portions of the sequence of the nucleic acid. A detectable change is brought about as a result of the hybridization of the oligonucleotides on the nanoparticles to the nucleic acid. The disclosure describes methods of synthesizing nanoparticle-oligonucleotide conjugates and methods of using the conjugates. The disclosure describes nanomaterials and nanostructures comprising nanoparticles and methods of nanofabrication utilizing nanoparticles. The disclosure describes a method of separating a selected nucleic acid from other nucleic acids.

SUMMARY

There is a need to form colloidal aggregates or cluster of particles in a controlled manner using inexpensive coating materials. Such clusters could be used in a variety of nonisotopic detection systems to increase the signal comprising fluorescence emission of high quantum yield. Such clusters may be used to provide tailored signal amplification that is not limited as to the chemical nature of the target molecule to be detected. It would be desirable that such non-isotopic probes could be used to bind target molecules of various and that they can be excited with a single excitation light source and with resultant fluorescence emissions with discrete fluorescence peaks.

Embodiments of the invention include nanocrystal aggregates. These compositions can include two or more aggregated nanocrystals; where the nanocrystals includes a coating layer, and the coating layer can include one or more imidazole groups. The coated nanocrystals interact or associate through their coating layers to form an aggregate.

The composition of aggregated nanocrystals may further include a cross linking agent. The aggregated nanocrystals can be crosslinked by one or more organophosphine compounds. The cross linking agent can include tris(hydroxymethyl)phosphine, beta-[tris(hydroxymethyl)phosphino] propionic acid, any combination of these, or other suitable organophosphine compounds.

The coating layer on the nanocrystals can be bound or operably linked to the nanocrystal by the one or more imidazole groups. The coating layer on the nanocrystals can include histidine, carnosine, polyhistidine, polyimidazole, glycyl histidine or other similar imidazole containing compounds. In some embodiments one or more imidazole groups of the coating layer bond or otherwise operably link the imidazole coating compound to the nanocrystal.

The aggregated nanocrystals can be luminescent, fluorescent, magnetic, or may include one or more these properties by aggregating two or more different nanocrystals that include any of these properties. In some embodiments, the aggregates can include nanocrystals that are semiconductor core nanocrystals or semiconductor core/shell nanocrystals.

The aggregate may further comprise at least one functional group on the surface of the aggregate. The aggregate may further comprise functional groups on the surface of the coated nanocrystal aggregate such as but not limited to hydroxyl, thiol, amino, acetylenic, carboxyl, ester, amide, dicarboxylic, carboxamide selenol, hydrazide, aldehyde, or combinations of any of these. The aggregates can be dispersed in a variety of organic solvents, mixtures of organic solvent and water, or in aqueous based solutions.

Embodiments of the invention can include aggregates that have been functionalized with reactive groups. A functionalized aggregate composition can include a nanocrystal aggregate and at least one affinity molecule. The nanocrystal aggregate comprises two or more coated nanocrystals; the nanocrystals comprise a coating layer comprising one or more imidazole groups where the nanocrystals interact through their coating layers to form an aggregate. In some embodiments, the aggregate may include at least one functional group on its surface with at least one affinity molecule is linked to the functional group.

In embodiments of the invention the affinity molecule can be but is not limited to a polyclonal antibody, a monoclonal antibody, a peptide, an aptamer, a nucleic acid, a polynucleotide, a lectin, a lipid, a small organic molecule, a polysaccharide, avidin, neutravidin, streptavidin, an avidin derivative, biotin, a biotin derivative, or any combination of these affinity molecules. The affinity molecule can be covalently linked to the functional group. The functional group can include but is not limited to hydroxyl, thiol, amino, carboxyl, ester, amide, dicarboxylic, carboxamide, selenol, hydrazide, aldehyde, or any combination of these.

Some embodiments of the invention can include an aggregate having a defined number of coated nanocrystals, coated nanoparticles, or any combination of these in the aggregate. The aggregate composition can include from about two or more to about twenty aggregated coated fluorescent semiconductor nanocrystals. The coated nanocrystals and or coated nanoparticles in the aggregate comprise a coating layer that includes one or more imidazole groups and the coated nanocrystals interact through their coating to form the aggregate. In some embodiments one or more imidazole groups of the coating layer bond or otherwise operably link the imidazole coating compound to the nanocrystals or nanoparticles. The number of coated nanocrystals, coated nanoparticles, or combination of these in the aggregate or cluster can separately form a cluster of a defined size, preferably between 2 and 20 coated nanocrystals of 2, 3, 4, 5, 6, 7, 8, 9, 10, 11, 12, 13, 14, 15, 16, 17, 18, 19, or 20 coated nanometer sized particles. The cluster or aggregate is a colloidal particle and the nanocrystals and/or nanoparticles in the aggregate can be crosslinked by an organophosphine compound.

One embodiment of the invention is a method of preparing aggregates comprised of coated nanocrystals. A method of preparing these aggregates can include the acts or steps of providing two or more nanocrystals, the nanocrystals include a coating layer comprising at least one imidazole group, and then contacting or combining the nanocrystals to prepare an aggregate coated nanocrystals. The nanocrystals interact through their coating layers to form the aggregate. The method can further include the act of placing the two or more nanocrystals in a solvent mixture and contacting or combining them to form an aggregate or an aggregate of a predetermined size. The solvent mixture can be an aqueous solvent mixture. Similar acts or steps can be used to prepare clusters or aggregates that include coated nanoparticles, or any combination of coated nanoparticles and coated nanocrystals where the coating layer comprises at least one imidazole group.

One embodiment of the invention is a method of using nanocrystal aggregates. The method can include detecting a target molecule in a sample with these nanocrystal aggregates. The method can include the acts of providing a sample suspected of containing a target molecule and providing one or more aggregates of coated nanocrystals to the sample. Preferably the nanocrystals are coated with a material with one or more imidazole groups and where the coating further includes an affinity ligand or other reactive functionality having binding specificity for the target molecule. Contacting the sample and the aggregates forms a treated sample. A treated sample can be excited with energy (electromagnetic radiation, an electric field and or magnetic field, high energy particles) and an excited complex formed that is used to detect the presence of a target molecule complexed with the aggregate in the treated sample. Similar acts or steps can be taken to use clusters or aggregates to detect target molecules where the aggregates include coated nanoparticles, or any combination of coated nanoparticles and coated nanocrystals where the coating layer comprises at least one imidazole group.

The detecting step or act can include detecting light emitted by the excited aggregate or cluster complex. The detecting step can include detecting light emitted by a nanocrystal aggregate complex with a radio labeled target molecule in a Scintillation Proximity assay. The detecting step or act may further include quantifying the amount of target molecule in the sample. In some embodiments, the energy used to excite the nanocrystals can have wavelength that is less than about 500 nm.

Embodiments of the present invention include fluorescent nanocrystals which have high fluorescence intensity and can for example be dispersed or solubilized in water or water containing solutions. The present invention provides for the synthesis of colloidal particles using functionalized fluorescent nanocrystal compositions. Embodiments of the invention provide methods for making and using these compositions in biological detection applications, material separations, and in the production of biosensors. The compositions are colloidal particles produced by clustering two or more nanocrystals and preferably two or more fluorescent nanocrystals together. The compositions and method for making them provides for colloidal fluorescent nanocrystal compositions which are water dispersible, chemically stable, and emit light with a high quantum yield and/or luminescence efficiency when excited with light or other sources of energy. The colloidal material, which comprises clusters or aggregates of coated nanocrystals, may also have chemical functional groups, compounds or ligands with moieties for bonding to target molecules and cells.

A highly luminescent, chemically functionalized, and water dispersible colloidal particle of clustered or aggregated coated nanocrystals in embodiments of the present invention may include a cluster of two or more nanocrystals, preferably those nanocrystals that have size dependent properties including fluorescent semi conductor nanocrystals, and more preferably fluorescent semiconductor nanocrystals coated with an organic coating. The coating on the fluorescent semiconductor nanocrystal is one that permits controlled aggregation of individual coated nanocrystals and the coating may be formed by complexation between the nanocrystal inorganic compound and organic material. Examples of such organic coatings include but are not limited to imidazole containing compounds like carnosine and histidine, polymers coating the nanocrystal including but not limited to imidazole (or an imidazole-mimicking compound) and phosphine or amine cross linking compounds.

The highly luminescent, chemically functionalized and water dispersible colloidal particle comprised of nanocrystals having a coating containing one or more imidazole groups in embodiments of the present invention can include those where the cluster is comprised of two or more quantum dots such as but not limited to a Group II-VI semiconductor material (of which ZnS, and CdSe are non-limiting illustrative examples), a Group III-V semiconductor material (of which GaAs is a non-limiting illustrative example), a Group IV semiconductor nanocrystal, colloidal gold, silver, ferromagnetic, ferrimagnetic nanoparticles, or any combination of these particles.

In the highly luminescent, chemically functionalized and water dispersible colloidal particles, aggregates of coated nanocrystals or clusters of coated nanocrystals, the cluster can include two or more core, core/shell, or a combination including these. The quantum dots may be chosen from an inorganic material such as but not limited to a Group II-VI semiconductor material (of which ZnS, and CdSe are illustrative examples), a Group III-V semiconductor material (of which GaAs is an illustrative example), a Group IV semiconductor material, colloidal gold, silver, ferromagnetic, ferrimagnetic nanoparticles, or a combination these. Preferably an organic material complexes with the inorganic material of the quantum dot by the formation of chemical adducts and bonds.

The adduct forming organic coating over the nanocrystals is preferably formed by an imidazole-containing compound (of which histidine, carnosine, polyhistidine, polyimidazole are illustrative examples), or an imidazole-mimicking compound (of which thiazole, oxazole, pyrrole, thiophene, furan, pyridine, pyrimidine, pyrazine, triazine, triazole, thiophene, phthalocyanine, porphyrin, and their derivatives are illustrative examples). Preferably the imidazole containing compound, or the imidazole mimicking compound in the coating is bonded to the nanocrystal through the imidazole or imidazole mimicking group. Optionally the organic coating may include and an alkyl phosphine-containing compound (of which tris(hydroxy methyl)phosphine and beta-[Tris(hydroxymethyl)phosphino]propionic acid are illustrative examples). The highly luminescent, chemically functionalized and water dispersible colloidal cluster particles, aggregates or clusters of coated nanocrystals, can have the imidazole-containing compound (or an imidazole-mimicking compound) and the alkyl phosphine containing compound crosslinked.

The highly luminescent, chemically functionalized, and water dispersible colloidal cluster particles preferably have a coating on the individual nanocrystals or the cluster that is functionalized so that the functionalized colloidal particle is capable of linking to a target molecule, affinity molecule, a sensor molecule or sensor substrate; and capable of, in response to excitation by a first energy, providing a second energy used for detection.

The target or affinity molecules linked to the colloidal aggregate of coated nanocrystals or cluster of coated nanocrystals may include but are not limited to those such as of polyclonal antibodies, monoclonal antibodies, a peptide, an aptamer, a nucleic acid, a lectin, a lipid, a small organic molecule, a polysaccharide, avidin, neutravidin, streptavidin, an avidin derivative, biotin, a biotin derivative. The target may also be a sensor surface diode, a nanodevice, an optical fiber, or any one of these whose surface has been functionalized to interact with reactive groups on the surface of the coating on the cluster.

The highly luminescent, chemically functionalized, and water dispersible colloidal particle, aggregate of coated nanocrystals or cluster of coated nanocrystals, may be used for detecting target molecules or surfaces including the acts of contacting one or more of the functionalized colloidal cluster particles with a sample (for example a molecule, cell, tissue, or substrate) being analyzed. The presence or absence of a target molecule or target substrate in the sample being determined by the affinity ligand on the cluster that has binding specificity for the molecule or substrate. If the target molecule or substrate is present in the sample a complex is formed comprising the functionalized colloidal particles bound to the substrate. Exposing the contacted sample in a detection system to a wavelength of light or a source of energy suitable for exciting the complexed functionalized colloidal cluster particles bound to the sample to emit a highly luminescent peak will signal the presence or absence of the target. The luminescence peak emitted by the complexes, if present, can be made by a detection system for detecting the luminescence peak; wherein the detection of luminescence peak is indicative of the presence of the target in the sample. For example, one detection method using the highly luminescent, chemically functionalized and water dispersible colloidal cluster particles for detection may include a detection system such as a luminescence counter used in a Scintillation Proximity assay.

Advantages of the present invention include enhanced brightness due to the effect of imidazole/THP (as in the case of standard functionalized nanocrystals) and multiple nanocrystals. Unlike embedded beads, colloidal fluorescent nanocrystals are coated with a thin transparent layer without fillers. This results in a minimum light shielding effect (inward and outward) and a brighter emission. Nanocrystals of different emissions can be clustered in one cluster particle with a unique signal (fingerprint) from the combination of the spectra of the clustered nanocrystals. The clusters of the present invention may be derivatized with carboxyl groups for covalent or electrostatic conjugation to a target protein or bioagent. Because the clusters include more than one nanocrystal, and unlike polymer embedded beads, they have high density and advantageously collection and separation by centrifugation is facilitated. Dual detection potential by visual (like colloidal gold) and/or fluorescent approaches can be used.

The above and other objects, features, and advantages of the present invention will be apparent in the following detailed description of the invention when read in conjugation with accompanying drawings in which reference numerals denote the same or similar parts throughout the several illustrated views and embodiments.

BRIEF DESCRIPTION OF THE DRAWINGS

The file of this patent contains at least one photograph or drawing executed in color. Copies of this patent with color drawing(s) or photograph(s) will be provided by the Patent and Trademark Office upon request and payment of necessary fee.

DETAILED DESCRIPTION OF THE INVENTION

Figure 1:
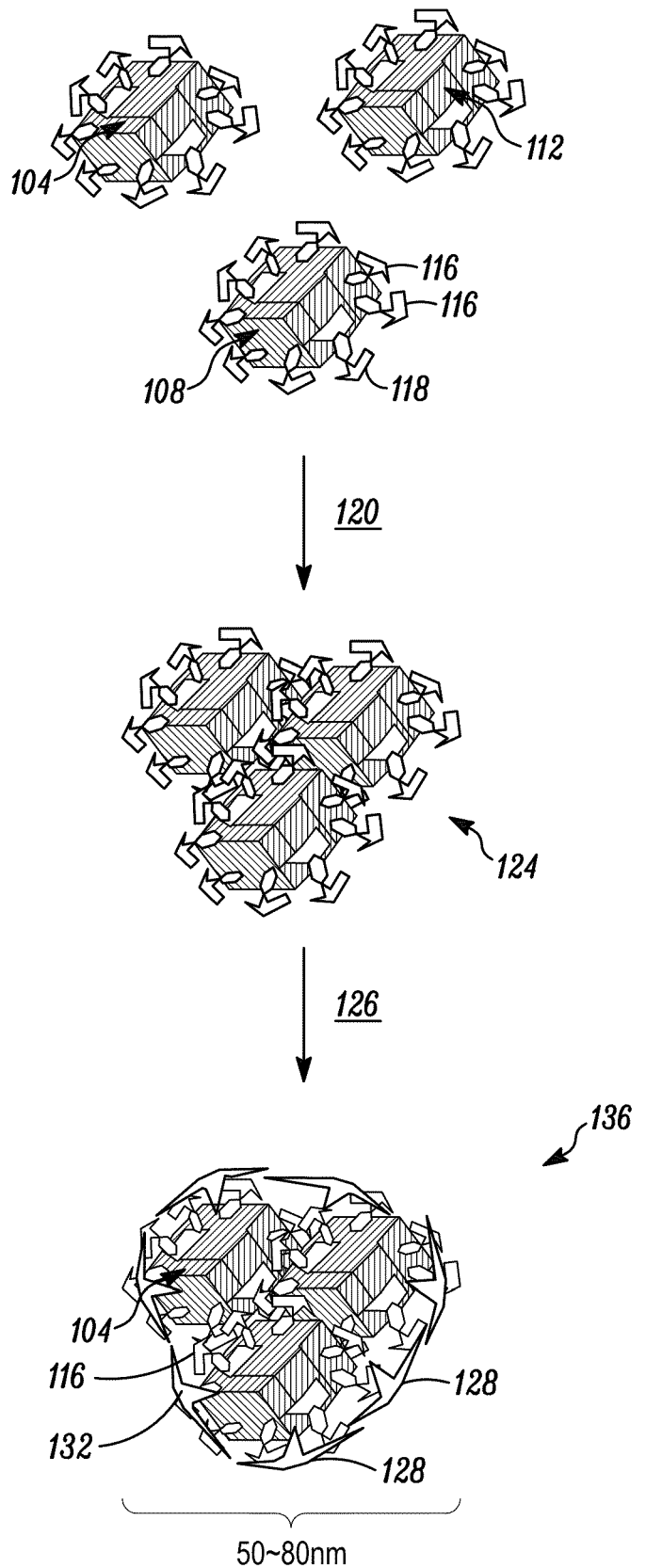
FIG. 1 Illustrates schematically the production of colloidal nanocrystals that are an aggregate of coated nanocrystals or a cluster of coated nanocrystals.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural references unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs or material is present and instances where the event does not occur or where the material is not present.

Throughout the specification of the application, various terms are used such as "primary", "secondary", "first", "second", and the like. These terms are words of convenience in order to distinguish between different elements, and such terms are not intended to be limiting as to how the different elements may be utilized.

Embodiments of the present invention are directed to nanocrystals with organic linkers or polymer coatings that are able to make the nanocrystals aggregate. While in preferred embodiments, the organic coating is an imidazole containing compound, the present invention is not limited to any particular coating disclosed, and any coating on the nanocrystals capable of forming aggregates of controlled size or a narrow distribution of sizes can be used.

Compositions of the invention can include colloidal particles produced by clustering two or more nanocrystals and preferably two or more fluorescent nanocrystals together. Colloidal aggregates or clusters in other embodiments of the present invention can be comprised of coated nanocrystals, coated nanoparticles, or any combination of these. A dispersion of coated nanocrystals, coated nanoparticles, or any combination of these can associate to form larger sized aggregates or clusters that include two or more coated nanocrystals, coated nanoparticles, or any combination of these.

The preparation of clusters of aggregated coated nanocrystals includes fluorescent nanocrystals or quantum dots coated with an organic shell or capping layer comprised of ligands formed by self assembly, where preferably the ligand bonds to the nanocrystal via a functional group of the ligand. Next, the induction of controlled aggregation of the coated nanocrystals is initiated. Clusters of aggregated coated nanocrystals (van der Waals type interaction) may be facilitated for example by using a solvent mixture that favors aggregation of the individually coated nanocrystals. Cross-linking and capping of the cluster can be used to link or bond together the individual nanocrystals in the cluster. The coated nanocrystals may also have their aggregation controlled or modified by functional groups on the coating compound. Similar materials and processes may be used to prepare clusters or aggregates of coated nanoparticles or aggregates that include any combination of coated nanoparticles and coated nanocrystals.

The preparation of nanocrystals of the present invention is illustrated with reference to nanocrystals coated by an imidazole ligand or imidazole mimicking ligand by self assembly, where preferably the ligand bonds to the nanocrystal via the imidazole or imidazole mimicking group. The coating of the nanocrystals and extraction from a solvent can be performed using the methods disclosed in U.S. Publication No. 2004-

0009341 A1 filed Sep. 17, 2002 Titled HIGHLY LUMINESCENT FUNCTIONALIZED SEMICONDUCTOR NANOCRYSTALS FOR BIOLOGICAL AND PHYSICAL APPLICATIONS the contents of which are incorporated into the present application by reference in their entirety. The induction of controlled aggregation of the coated nanocrystals is initiated to form clusters of coated nanocrystals (van der Waals type interaction) using for example a solvent mixture like 50% ethanol/50% water (the ratio of ethanol to water can be used to determine the final size of the colloidal particle). The number of nanocrystals per particle (i.e., the size of the formed particle) can be manipulated by changing the ratio of ethanol. Larger particles can be formed by adding higher concentrations of ethanol. For approximately 80 nm size (5-10 nanocrystals per particle), 50% of ethanol (final concentration) can be used. Other solvents or mixtures of solvents may be used to initiate the controlled aggregation of the coated nanocrystals to form the clusters. Finally, surface oriented cross-linking and capping of the cluster can be used to link or bond together the individual coated nanocrystals. The imidazole coated nanocrystals or nanocrystals coated by imidazole mimicking compound may also have their aggregation controlled or modified by functional groups on the coating compound. Advantageously, the coating compounds of the present invention do not require that the nanoparticles be further functionalized with individual recognition groups that are complementary to each other, have recognition groups that are not complementary but bridged through a bispecific linker, or require a bivalent linker that recognizes the surface of one or more nanoparticles and is used for aggregation— this simplifies the process for making clusters. Preferably the imidazole coated nanocrystals or nanocrystals coated by imidazole mimicking compound are those that can be linked together to form the cluster by a compound such as but not limited to tris(hydroxy methyl)phosphine or other cross linking compounds disclosed in U.S. Ser. No. 10/410,108, filed Apr. 9, 2003, titled HIGHLY LUMINESCENT FUNCTIONALIZED SEMICONDUCTOR NANOCRYSTALS FOR BIOLOGICAL AND PHYSICAL APPLICATIONS, the contents of which are incorporated by reference in their entirety into the present application.

FIG. 1 illustrates an embodiment of a composition of the present invention and a method for making it. Nanocrystals and/or nanoparticles 104, 108, and 112, which can be the same or different, include a ligand coating that comprises one or more coating molecules 116 and or 118 operably linked with each nanocrystal or nanoparticle. The molecules 116 and or 118 can optionally have reactive functionalities to link with target molecules, affinity molecules or cross-linking agents. The coated nanocrystals can aggregate 120 by adjusting the concentration of solvents that suspend the coated nanocrystals or nanoparticles. The suspended particles aggregate to form a colloidal cluster 124 of the coated nanocrystals and or coated nanoparticles interacting or associated through their coating. The colloidal cluster or aggregate 124 can be optionally crosslinked 126 to form a crosslinked colloidal cluster or aggregate 136. For example, one or more crosslinking molecules 128 and or 132 can be used to operably link the coated nanocrystals in the aggregate 124 together. The cross linking molecules 128 and or 132 can be the same or different and can have reactive functionalities to link the aggregate 136 to one or more linking groups, affinity groups, target molecules, or a substrate.

One embodiment of the invention is a composition comprising one or more colloidal particles. The colloidal particle can include of two or more fluorescent semiconductor nanocrystals. Each fluorescent semiconductor nanocrystal is coated with an organic shell that can be formed by complexation between the fluorescent semiconductor nanocrystal and an imidazole containing molecule and an optional organophosphine compound. In the coating, one or more imidazole groups from the imidazole containing molecule are bonded to the fluorescent semiconductor nanocrystal. The coated fluorescent semiconductor nanocrystals aggregate or form a colloidal cluster that can optionally be bonded to each other in the colloid by an organophosphine containing compound. The size of the colloid can be modified by controlled aggregation of two or more imidazole containing compound coated fluorescent semiconductor nanocrystals. In some embodiments, the colloid is a cluster or aggregate of coated nanocrystals that is comprised of two or more quantum dots or semiconductor nanocrystals. In some embodiments, the colloidal particle or aggregate of coated nanocrystals is comprised of two or more core or core/shell quantum dots or core/shell semiconductor nanocrystals. The colloidal particle or aggregate comprised of coated nanocrystals can be luminescent. In some embodiments of the composition, the colloid cluster or nanocrystal aggregate includes more than 3, 4, 5, 6, 7, 8, 9 or more than 10 quantum dots or semiconductor nanocrystals.

The clusters may include two or more coated nanocrystals, coated nanoparticles, or any combination of these linked together. Dimers, trimers, and large n-mers may be formed where n is an integer 2 or larger, preferably from 2, 3, 4, 5, 6, 7, 8, 9, 10, 11, 12, 13, 14, 15, 16, 17, 18, 19, or 20, and most preferably from about 2, 3, 4, 5, 6, 7, 8, 9 or 10. Where a distribution of sizes for cluster occurs, the size of the cluster can be further selected for example by size selective precipitation or sieving filtration.

The term nanocrystal refers to an inorganic crystallite having a largest dimension of from between about 1 nm and about 1000 nm, more typically between about 2 nm and about 20 nm including but not limited to doped metal oxide, semiconductor, and doped semiconductor nanocrystals. A semiconductor nanocrystal or quantum dot is capable of emitting electromagnetic radiation upon excitation (i.e., the semiconductor nanocrystal is luminescent) and includes a core of one or more first semiconductor materials, and may be surrounded by a shell of a second semiconductor material. Preferably the coated nanocrystals are fluorescent nanocrystals. A semiconductor nanocrystal core surrounded by a semiconductor shell is referred to as a "core/shell" semiconductor nanocrystal. The surrounding "shell material typically has a bandgap energy that is larger than the bandgap energy of the core material and can be chosen to have an atomic spacing close to that of the core substrate. The core and/or shell can be a semiconductor material including, but not limited to, those of the Groups II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like), and alloys or mixtures thereof.

Nanoparticle refers to particles less than 1000 nm in size which may include regions that are semicrystalline amorphous, any combination of these regions, or any combination of these regions that further includes crystalline regions. The association between the coated nanocrystals, coated nanoparticles, or any combination of these in an aggregate or cluster can be through a variety of chemical, physical, or a combination of these bonding interactions including but not limited to one or more of: covalent, ionic, hydrogen bonding, van der Waals, chemisorption, physisorption, and the like.

Colloidal aggregates or colloidal clusters in embodiments of the present invention can be comprised of coated nanocrystals, coated nanoparticles, or any combination of these. The coated nanocrystals and or nanoparticles may be semiconductors, metallic, magnetic, or ceramic materials. The clusters of aggregated coated nanocrystals, coated nanoparticles, or any combination of these may include those having fluorescent, luminescent, ferromagnetic, antiferromagnetic, ferrimagnetic, antiferrimagnetic or superparamagnetic properties.

In embodiments of the aggregate or cluster compositions the coating on the nanocrystals or nanoparticles includes an imidazole containing molecule or an imidazole containing compound. In some embodiments of the composition, the coating material on the nanocrystals or nanoparticles that is used to aggregate or flocculate them is comprised of an imidazole-containing compound (of which histidine, carnosine, polyhistidine, polyimidazole are illustrative examples), or an imidazole-mimicking compound (of which thiazole, oxazole, pyrrole, thiophene, furan, pyridine, pyrimidine, pyrazine, triazine, triazole, thiophene, phthalocyanine, porphyrin, and their derivatives are illustrative examples). Coatings in embodiments of the present invention may include imidazole and imidazole mimicking compounds with more than one imidazole group. For example, a di-imidazole called 1,1'-carbonyldiimidazole (or Wang imidazolide carbamate resin) that can be used to induce aggregation. Another example includes the imidazole compound called 4-imidazoleacrylic acid (or urocanic acid) that can be polymerized by heat or other polymerization initiators to induce nanocrystal aggregation.

In some embodiments of the composition, the aggregated coated nanocrystals, aggregated coated nanoparticles, or aggregated coated nanocrystals and aggregated coated nanoparticles are bonded or crosslinked one to the other in the colloid by an organophosphine containing compound. In some embodiments the imidazole-containing compound (or an imidazole-mimicking compound) and an alkyl phosphine containing compound are bonded by crosslinking. In some embodiments the aggregated coated quantum dots can be cross linked with an alkyl phosphine-containing compound such as tris(hydroxy methyl)phosphine, or beta-[Tris(hydroxymethyl)phosphino]propionic acid. Various trivalent and/or bivalent linkers may be used in coating the nanocrystals or nanoparticles. For example, controlled aggregation of nanometer sized particles may be achieved by using trivalent crosslinkers like TSAT (Tris-succinimidyl aminotriacetate) and THP (Tris(hydroxymethyl)phosphine).

Embodiments of the aggregated coated nanocrystals, aggregated coated nanoparticles, or aggregated coated nanocrystals and aggregated coated nanoparticles are capable of, in response to excitation by a first energy, providing a second energy used for detection. These colloidal aggregates can be optionally cross linked, and can have functional groups on a surface of the colloid aggregate capable of linking to target molecules, affinity molecules, a sensor surface, a well plate, surface of a diode, a MEMS sensor, an optical fiber, or to other similar molecules and substrates. The target or affinity molecules can separately include but are not limited to polyclonal antibodies, monoclonal antibodies, peptides and polypeptides, an aptamer, a nucleic acid or polynucleotide, a lectin, a lipid, a small organic molecule, a polysaccharide, avidin, neutravidin, streptavidin, an avidin derivative, biotin, a biotin derivative, or other affinity and target groups.

A method of using chemically functionalized and water dispersible, colloidal clusters of coated nanocrystals and or coated nanoparticles in a detection system can include the acts of contacting the functionalized colloidal cluster particles with a sample being analyzed for the presence or absence of a substrate or target molecule for which an affinity ligand on the colloidal cluster has binding specificity. If the substrate or target molecule is present in the sample, a complex is formed comprising the functionalized colloidal cluster particles bound to the substrate. The method can include exposing the complex, if formed, in the detection system to a wavelength of light or a source of energy that causes the functionalized colloidal particles of the complexes to emit a second energy. In some embodiments, the second energy can be a highly luminescent peak emitted by colloidal clusters comprising coated fluorescent core/shell semiconductor nanocrystals. The method can further include detecting the second energy which indicates the presence of the target or substrate. For example, the luminescence peak emitted by the complexes of colloidal clusters comprising coated fluorescent core/shell semiconductor nanocrystals bound to a target, can be used to indicate the presence of the target molecule. In some embodiments, the aggregate or cluster may be excited with a single excitation light source and with resultant fluorescence emissions with discrete fluorescence peaks detected.

Excitation sources suitable for characterizing aggregates or clusters with one or more coated nanocrystals, coated nanoparticles, or a combination of these optionally linked to one or more target molecules or substrates in various embodiments of this invention can include but are not limited to polychromatic ultraviolet and visible lamps, substantially monochromatic sources of light, polarized light, beta emitters including but not limited to $^{33}P$, $^{125}I$, and $^{3}H$. Sources of light may include low, medium, and high pressure lamps as well as lasers. In some embodiments the energy used to excite the nanocrystals or nanoparticles can have wavelength that is less than about 500 nm. Electric current and electron bombardment of the nanocrystals or nanoparticles may also be used for excitation. One energy source can be an alternating magnetic field generator for producing an alternating magnetic field that may be guided to a specific location (well plates, a tissue sample, or location within a patient) by a magnetic circuit. Suitable detectors may include but are not limited to visual detection, photodiodes, photomultipliers, heat detectors and charge coupled device detectors (CCDs); detectors may also include the use of polarizing filters. The emission of light and its intensity from excited functionalized fluorescent nanocrystals in colloidal aggregates and clusters may be measured in any direction with respect to the excitation source; preferably the emission intensity is measured parallel, perpendicular, or in both directions with respect to the excitation source. The location and concentration of nanocrystal and or nanoparticle aggregates that include one or more coated ferromagnetic, antiferromagnetic, ferrimagnetic, antiferrimagnetic or superparamagnetic nanoparticles or nanocrystals may each be determined using an existing technique, such as magnetic resonance imaging, or another diagnostic technique can be established and performed using a suitable magnetometer, such as a Superconducting Quantum Interference Device (SQUID).

The detecting step or act can include detecting light or energy emitted by the excited complex. The detecting step or act may include detecting the magnetic flux and or energy such as light emitted from an aggregate or cluster with one or more coated fluorescent nanocrystals, one or more coated nanocrystals, one or more coated nanoparticles, or any combination of these.

In one embodiment, the detection step or act can include using an aggregate or cluster with one or more coated fluorescent nanocrystals in a Scintillation Proximity assay. For example, a target molecule may include a site that can react with a radiolabel. The aggregated nanocrystal with an affinity group for the target molecule can act as a scintillant and emit light when the radiolabeled target molecule bonds or associates with the aggregate or cluster with one or more coated fluorescent nanocrystals. When the radiolabeled target molecules forms a complex with the aggregate or cluster with one or more coated fluorescent nanocrystals, then light characteristic of the fluorescent nanocrystal is emitted from the aggregate. For example, a biotinylated target peptide with a phosphorylation site may be radiolabeled using an enzyme with a [$\gamma$-$^{33}$P] source and combined with a streptavidin affinity group linked to an aggregate or cluster with one or more coated core shell fluorescent nanocrystals. The $^{33}$P labeled peptide can excite the aggregate or cluster with one or more coated core shell fluorescent nanocrystals to emit light which can be detected. The detecting step or act may further include quantifying the amount of target molecule in the sample.

Kits with one or more compositions that include an aggregate or colloidal cluster with one or more coated fluorescent nanocrystals, one or more coated nanocrystals, one or more coated nanoparticles, or any combination of these are provided. Kits with compositions that include colloidal sized cluster or aggregates may be used to detect target molecules (for example by hybridization) or they can be used for various diagnostic purposes or microarray analysis. Such colloidal sized aggregate or cluster with one or more reactive functionalities or affinity molecules may be bound directly or indirectly (for example by hybridization) to one or more solid supports or one or more arrays. These bound colloidal sized aggregates or bound colloidal clusters may be included with the kit. The kits containing these colloidal aggregates or clusters may include one or more blank solid supports or one or more arrays that can be functionalized or impregnated with colloidal aggregates or target substrates.

The kits can be used with embodiments of the methods of the invention. The kits can be used for detecting target molecules or other substrates. The kits may include one or a number (for example two, three, four or more) of different types of colloidal aggregate or colloidal cluster with one or more coated fluorescent nanocrystals. Each type of aggregate or cluster may include different coated fluorescent nanocrystals and or functional groups and or affinity molecules. These may be stored (in one or more separate containers). The kits of the invention may also comprise, in the same or different containers, at least one component selected from one or more DNA polymerases (preferably thermostable DNA polymerases), one or more primers, one or more templates, a suitable buffer, enzymes (for example but not limited to a kinase), a combination of these or other reagents.

The following examples will serve to illustrate various embodiments of the present invention, but should not be construed as a limitation in the scope thereof. One skilled in the art will appreciate that although specific reagents and conditions are outlined in the following examples, modifications can be made which are meant to be encompassed by the spirit and scope of the invention.

Example 1

This example illustrates the preparation of colloidal nanocrystals (cluster of aggregated coated nanocrystals).

2 mg of CdSe/ZnS core/shell nanocrystals were suspended in an organic solvent (e.g., pyridine) were extracted by 1.6 ml of 500 mM imidazole containing compound (e.g., Gly-His). After adding chloroform (5 volumes of pyridine), the preparation was slowly mixed by a rotary mixer for 30 minutes. The upper aqueous layer was transferred to a different tube and diluted with 6 ml of distilled water. Then, the preparation was dialyzed against distilled water through a 10 kD for 70 minutes. Following dialysis, 10% v/w of glycerol is added. To the resulting solution equal volume of absolute ethanol was added. The number of nanocrystals per particle (i.e., the size of the formed particle) could be manipulated by changing the ratio of ethanol. Larger particles could be formed by adding higher concentrations of ethanol. For about 80 nm size (5-10 nanocrystals per particle), 50% of ethanol (final concentration) was used. After 10 minutes, 5 mM of tris-(hydroxymethylphosphine) (THP) was added to the preparation and then the solution was mixed for 15 hours at room temperature using a rotary mixer. The THP treatment was repeated one time using the same conditions. A semi-transparent solution was formed. The colloidal nanocrystals were finally washed using centrifugation filters (MWCO 10 kD) and re-suspended in the desired buffer.

Example 2

This example illustrates the preparation of colloidal cluster of aggregated coated nanocrystals conjugated to avidin.

A probe molecule having a free carboxyl-reactive group may be operably linked to a molecule of an alkyl phosphine- or imidazole-containing compound including the coating of the colloidal particle (cluster of aggregated coated nanocrystals) using methods known in the art (e.g., treatment with EDC (1-ethyl-3-[3-dimethyl-aminopropyl]carbodiimide), followed by treatment with sulfo-NHS (sulfo-N-hydroxysuccinimide)).

Alternatively a probe molecule having a free amine-reactive group may be operably linked to molecule of an alkyl phosphine- or imidazole-containing compounds comprising the colloidal particle (cluster of aggregated coated nanocrystals) using methods known in the art (e.g., treatment with EDC (1-ethyl-3-[3-dimethyl-aminopropyl]carbodiimide), followed by treatment with sulfo-NHS (sulfo-N-hydroxysuccinimide).

The avidin was operably linked using these reactions to the colloidal nanocrystals (cluster of aggregated coated nanocrystals) previously prepared (Example 1) to form a complex. Procedures similar to these were also used to operably bond functionalized fluorescent nanocrystals in the cluster of aggregated coated nanocrystals from Example 1 to the following: ConA, lectin, IgG, and nucleic acids. The colloidal nanocrystals (cluster of aggregated coated nanocrystals) comprising a 4-8 nanocrystals per particle (produced by the methods described in Example 1 herein), were operably bound to avidin. The amino groups of avidin were operably bound to the carboxyl groups of the colloidal nanocrystals (cluster of aggregated coated nanocrystals).

1 mg of colloidal nanocrystals (cluster of aggregated coated nanocrystals) suspended in 2 ml conjugation buffer (MES 50 mM, NaCl 250 mM was treated by 2 mM of EDC and 5 mM sulfo NHS. The resulting solution was mixed at room temperature for 15 minutes, and then was dialyzed against the conjugation buffer for 90 minutes using dialysis membrane with a molecular weight cut off (MWCO) of 10,000 daltons. To the resulting solution was added 100-200 microgram avidin (dissolved in 500 ul conjugation buffer), and the entire solution was mixed at room temperature for 30 minutes. The reaction was terminated by adding 25 mM glycine and mixing for another 30 minutes. The solution was then purified from excess avidin and reagents using ultrafiltration centrifugal membranes with a MWCO of 10 KD.

Example 3

This example illustrates the covalent linking of colloidal biocrystals (cluster of aggregated coated nanocrystals) to avidin.

Activation of carboxyl groups on colloidal nanocrystals (cluster of aggregated coated nanocrystals) as prepared in Example 1. In a 1.5 ml tube 1 ml of colloidal nanocrystals (1 ml 100 ug/ml of colloidal nanocrystals (cluster of aggregated coated nanocrystals) were briefly vortexed in a linking buffer (MES (50 mM), NaCl (200 mM), pH 6.7) with 0.05% Tween-20) for about 5 seconds to ensure uniform suspension.

Added to the colloidal nanocrystals (cluster of aggregated coated nanocrystals) was 100 µl EDC (1-Ethyl-3-(3-Dimethylaminopropyl)carbodiimide Hydrochloride, Pierce) 20 mM in water, freshly prepared before use, and 100 ul Sulfo-NHS (freshly prepared Sulfo-NHS, (Pierce)) 50 mM in water to obtain a final concentration of 2 mM and 5 mM, respectively for EDC and Sulfo-NHS. Then, this was incubated with mild mixing at room temperature for 10 minutes manually (a rotary mixer could also be used).

Linking reaction: The excess of EDC and Sulfo-NHS was removed by 10 kD MWCO dialysis (Slide-A-Lyzer (MWCO 10,000 Daltons; Pierce) against the linking buffer (MES (50 mM), NaCl (200 mM), pH 6.7) with 0.05% Tween-20 for 70 to about 90 minutes (final volume of colloidal nanocrystal (cluster of aggregated coated nanocrystals) solution is 1.2 ml).

Then the suspension was transferred from the dialysis cassette into a 15 ml tube and agitated by adding 200 µl avidin solution (20-40 µg Avidin in 200 µl of linking buffer with 0.05% Tween-20 (Sigma)). This was incubated for about 1 hour at room temperature with mild mixing. An incubation time was determined for each ligand; to determine activity and preferred conditions for linking different ligands to the cluster of aggregated coated nanocrystals.

The reaction with glycine was quenched at a final concentration of 10 mM (for 1.4 ml add 14 µl of a 1 M glycine solution) and final pH was adjusted to 7.5 by sodium carbonate (about 10 µl of 1M $Na_2CO_3$ for 1.4 ml) and mixing continued for an additional 30 minutes.

The mixture was transferred into a 4 ml Millipore centrifugation filter (MWCO 10 k) and TBS was added with 0.05% Tween-20 up to 4 ml, and was mixed and spun at 2000 rpm/5 min. The supernatant was then carefully removed to a different collection tube. The fluffy sediment was resuspended in TBS with 0.05% Tween-20 and spun at 2000 rpm for about 5 min. The supernatant was carefully removed and it was pooled with the first supernatant. Finally, the fluffy sediment was resuspended with a suitable volume (about 1 ml) of TBS with 0.05% Tween-20 and stored at 4° C. until its use.

The concentration of protein can be determined by determining the 280 nm absorbance of the pooled supernatants and calculating the conjugated fraction.

For other targets or proteins, the suitable amounts for conjugation can be determined empirically. The MW of avidin is about 65 kD. For antibodies (MW about 150 kD), replacing the same number of molecules can be used. For example, instead of 20-40 µg it might be suitable to start with 50-100 µg of antibodies to match with 100 µg colloidal nanocrystals (cluster of aggregated coated nanocrystals).

Example 4

This example shows the detection of biotin target antigens with avidin-conjugated nanocrystal colloids (avidin conjugated cluster of aggregated coated nanocrystals).

Colloidal cluster biotin-conjugated (target) and unconjugated (negative control) antibodies on nitrocellulose in a range of concentrations from 1 µg to 30 ng were placed on sheets in 6 well plates.

The sheets were rinsed with TBS with 0.1% Tween. The TBS was blocked in with 0.1% Tween with 1% Perfect Block (MoBiTec) for 1 hour at room temperature. The avidin-conjugated cluster colloids were diluted to 5 µg/ml in a blocking solution. As a positive control, one can dilute avidin-conjugated FITC (Sigma) in the same manner.

Figure 2:
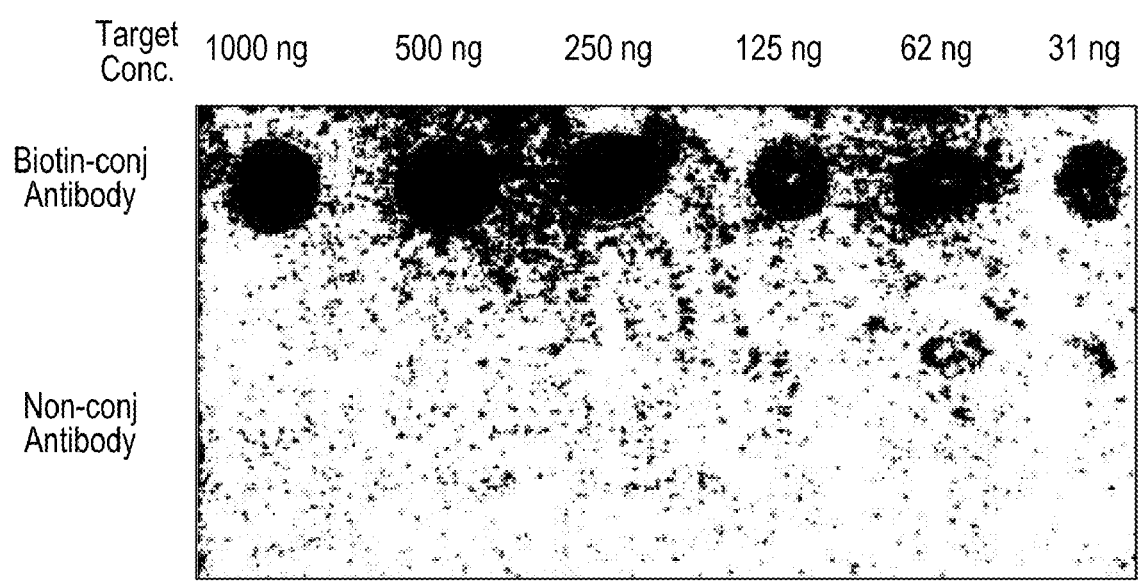
FIG. 2 Shows test results where colloidal nanocrystals, comprised of an aggregate of coated nanocrystals or a cluster of coated nanocrystals, were conjugated to avidin using EDC chemistry and were tested by dot blot assay to detect biotinylated antibody blotted on nitrocellulose membrane; the top row is the biotinylated antibodies and the bottom row is the non biotinylated antibodies (control).

2 ml of the fluorescent conjugate was added to each well and incubated for 1 hour at room temperature without agitation. This was then rinsed 3 times using TBS with 0.1% Tween while avoiding the application of the rinse buffer directly onto the nitrocellulose. The membranes were then illuminated with UV light from above. The colloids appeared orange without UV illumination. FIG. 2 shows the test results where colloidal nanocrystals were conjugated to avidin using EDC chemistry and were tested by dot blot assay to detect biotinylated antibody blotted on a nitrocellulose membrane; the top row was the biotinylated antibodies and the bottom row was the non biotinylated antibodies (control). Binding to the top row of dots were specific avidin-biotin interaction; binding to the lower row of dots indicated the presence of unconjugated colloidal clusters. The same buffers and reagent concentrations can be used in a lateral flow assay system, or to detect biotinylated antigens in a Western Blot.

Example 5

This example illustrates the functionalization or coating of core-shell nanocrystals that was used to form colloids (cluster of aggregated coated nanocrystals).

500 mM Gly-His was dissolved TTin 1M $Na_2CO_3$. Sonnicat The core-shell nanocrystals were sonicated and then 2 mg core-shell nanocrystals were added to Gly-His solution in an inert atmosphere. Then 6 ml chloroform about 3 ml/mg NCs was added and extracted for 30 min. on a rotator platform at room temperature. A centrifuge was then used for 2 minutes at 500 rpm. The top layer was then removed to a 50 ml tube. Then the interface was removed to eppendorf tubes and a centrifuge was used for 1 minute at 6000 rpm. The top layer was collected and added to previously collected material. (Total recovery about 1 ml). 5 ml $ddH_2O$ was added and dialyzed in a 10 kD MWCO Slide-Lyzer against 2 L $ddH_2O$ for 70 minutes at room temperature. The dialyzed material was then moved to a 50 ml tube and 12 ml 95% EtOH/5% Isopropanol was added quickly while vorxeting and mixed gently 10 minutes. 4 mg $H_2N$-PEG-COOH (Nektar, mw 3,400) was added and then mixed gently 3 minutes. Glycerol was then added to a final concentration of 10% and the pH was adjusted to 9.0+/−0.5 with 1M Citric Acid. The tube was then filled with argon and sonicated for 5 minutes. 5 mM THP (freshly made) was added and incubated on rotator platform overnight (while protecting from light). 5 mM THP (freshly made) was then added and incubated on rotator platform overnight (while protecting from light). A Centrifuge was used for 2 minutes at 500 rpm in an Amicon filter (10 kD MWCO). Do not allow a true pellet to prevent aggregation of the colloids. The supernatant (check to be sure it is not fluorescent) was removed. Resuspend pellet in $ddH_2O$ and use a centrifuge 2 minutes at 500 rpm. The colloids were resuspended in a desired buffer.

What is claimed is:

1. A method of preparing a nanocrystal aggregate, comprising:

contacting two or more nanocrystals in a solvent, the nanocrystals comprising a coating layer comprising at least one imidazole group;

contacting the nanocrystals to prepare an aggregate of coated nanocrystals;

controlling the aggregate size by modifying the solvent; and cross-linking the aggregate.

2. The method of claim 1, wherein the nanocrystals interact through their coating layers.

3. The method of claim 1, wherein the contacting step further comprises placing the two or more nanocrystals in a solvent mixture.

4. The method of claim 3, further comprising adjusting the concentration of solvents in the solvent mixture.

5. The method of claim 1, wherein the size of the aggregate is about 50-80 nm.

6. The method of claim 1, wherein the aggregate comprises about 2 to about 20 coated nanocrystals.

7. The method of claim 1, wherein the coating layer comprises a compound selected from histidine, carnosine, glycyl histidine, polyhistidine, polyimidazole, 1,1'-carbonyldiimidazole and 4-imidazoleacrylic acid.

8. The method of claim 1, wherein the coating layer comprises a compound selected from thiazole, oxazole, pyrrole, thiophene, furan, pyridine, pyrimidine, pyrazine, triazine, triazole, thiophene, phthalocyanine, porphyrin and derivatives thereof.

9. The method of claim 1, wherein the two or more nanocrystals are semiconductor nanocrystals.

10. A method of preparing a nanocrystal aggregate, comprising:

contacting two or more nanocrystals in a solvent, the nanocrystals comprising a coating layer comprising at least one imidazole group;

contacting the nanocrystals to prepare an aggregate of coated nanocrystals;

controlling the aggregate size by modifying the solvent; and cross-linking the aggregate, wherein the contacting step further comprises placing the two or more nanocrystals in an aqueous solvent mixture, wherein the aqueous solvent mixture further comprises ethanol.

* * * * *